United States Patent
Caneau et al.

(10) Patent No.: US 9,455,551 B2
(45) Date of Patent: Sep. 27, 2016

(54) MID-IR MULTIWAVELENGTH CONCATENATED DISTRIBUTED-FEEDBACK LASER WITH AN ACTIVE CORE MADE OF CASCADED STAGES

(71) Applicant: Thorlabs Quantum Electronics, Inc., Jessup, MD (US)

(72) Inventors: Catherine Genevieve Caneau, Corning, NY (US); Feng Xie, Painted Post, NY (US); Chung-En Zah, Holmdel, NJ (US)

(73) Assignee: Thorlabs Quantum Electronics, Inc., Jessup, MD (US)

( * ) Notice: Subject to any disclaimer, the term of this patent is extended or adjusted under 35 U.S.C. 154(b) by 0 days.

(21) Appl. No.: 14/371,513

(22) PCT Filed: Jan. 11, 2013

(86) PCT No.: PCT/US2013/021102
§ 371 (c)(1),
(2) Date: Jul. 10, 2014

(87) PCT Pub. No.: WO2013/106619
PCT Pub. Date: Jul. 18, 2013

(65) Prior Publication Data
US 2015/0008327 A1 Jan. 8, 2015

Related U.S. Application Data

(60) Provisional application No. 61/586,327, filed on Jan. 13, 2012.

(51) Int. Cl.
*H01S 5/34* (2006.01)
*G01N 21/39* (2006.01)
(Continued)

(52) U.S. Cl.
CPC .............. *H01S 5/3425* (2013.01); *B82Y 20/00* (2013.01); *G01N 21/39* (2013.01); *G01N 21/47* (2013.01);
(Continued)

(58) Field of Classification Search
CPC .............. H01S 5/3402; H01S 5/1215; H01S 5/06258; H01S 5/3425; G01N 21/59; G01N 21/39; G01N 21/47; G02B 6/102
USPC ....................................... 250/341.8
See application file for complete search history.

(56) References Cited

U.S. PATENT DOCUMENTS 5,077,752 A * 12/1991 Tada et al. ..................... 372/96
6,215,804 B1 * 4/2001 Sahlen et al. .............. 372/50.11
(Continued)

FOREIGN PATENT DOCUMENTS

| CN | 1237298 A | 12/1999 |
| JP | 63147388 A | 6/1988 |
| WO | 9810544 A2 | 3/1998 |

OTHER PUBLICATIONS

Li W et al; "Multiwavelength Gain-Coupled DFB Laser Cascade: Design Modeling and Simulation", IEEE Journal of Quantum Electronics, IEEE Service Center, Piscataway, NJ, USA, vol. 36, No. 10, Oct. 1, 2000 (200-10-01), pp. 1110-1116, XP011449762, ISSN: 0018-9197, DOI: 10.1109/3.880650 Abstract; figures 1, 10.
(Continued)

*Primary Examiner* — Marcus Taningco
(74) *Attorney, Agent, or Firm* — Graham Curtin, P.A.

(57) ABSTRACT

Concatenated distributed feedback lasers having multiple laser sections laid out in series are disclosed. The concatenated distributed feedback lasers utilize quantum cascade core designs to produce optical gain in the mid-infrared region and may generate several wavelengths simultaneously or sequentially. Methods of making along with methods of using such devices are also disclosed.

17 Claims, 4 Drawing Sheets

(51) Int. Cl.

| | |
|---|---|
| *H01S 5/0625* | (2006.01) |
| *H01S 5/10* | (2006.01) |
| *B82Y 20/00* | (2011.01) |
| *G01N 21/47* | (2006.01) |
| *G01N 21/59* | (2006.01) |
| *H01S 5/12* | (2006.01) |
| *H01S 5/028* | (2006.01) |

(52) U.S. Cl.
CPC ........... *G01N 21/59* (2013.01); *H01S 5/06256* (2013.01); *H01S 5/1096* (2013.01); *G01N 2201/0612* (2013.01); *H01S 5/0287* (2013.01); *H01S 5/1215* (2013.01); *H01S 5/3402* (2013.01)

(56) References Cited

U.S. PATENT DOCUMENTS

| | | | | |
|---|---|---|---|---|
| 6,608,855 | B1* | 8/2003 | Hwang et al. | 372/96 |
| 6,810,053 | B1* | 10/2004 | Botez et al. | 372/45.01 |
| 6,826,223 | B1* | 11/2004 | Meyer et al. | 372/96 |
| 7,177,335 | B2* | 2/2007 | Kamp et al. | 372/46.01 |
| 2005/0276298 | A1* | 12/2005 | Fischer et al. | 372/50.1 |
| 2008/0037608 | A1* | 2/2008 | Zhou et al. | 372/50.11 |
| 2008/0151956 | A1* | 6/2008 | Kim et al. | 372/45.01 |
| 2011/0255089 | A1* | 10/2011 | Bhatia | G01B 11/00 356/400 |
| 2011/0286477 | A1* | 11/2011 | Kuksenkov | G02F 1/3532 372/22 |

OTHER PUBLICATIONS

Straub, A, et al; "Simultaneously at two wavelengths (5.0 and 7.5 μm) singlemode and tunable quantum cascade distributed feedback lasers". Electronics Letters, IEEE Stevenage, GB, vol. 38, No. 12, Jun. 6, 2002, pp. 565-567, XP006018272, ISSN: 0013-5194, DOI: 10.1049/EL: 20020355 the whole document.

Talneau A et al: "Constant Output Power and Low Linewidth Ina Simple Wide-Tuning DFB Laser With Multiwavelength Grating" IEEE Journal of Selected Topics in Quantum Electronics,US, IEEE Service Center, Piscataway, NJ, US, vol. 3, No. 2, Apr. 1, 1997, pp. 628-631, XP000735963 ISSN: 1077-260X, DOI: 10.1109/2944. 605714 abstract; figure 1.

Namjou, K et al: "Sensitive Absorption Spectroscopy with a Room-temperature Distributed-feedback Quantum-cascade Laser", Optics Letters, OSA, Optical Society of America, Washington, DC, US, vol. 23, No. 3, Feb. 1, 1998, pp. 219-221, XP000741217, ISSN: 0146-9592 Abstract; figure 1.

Straub, A, et al; Two-wavelength quantum cascade lasers with heterogeneous cascades. Optoelectronic and Microelectronic Materials and Devices, 2002 Conference on Dec. 11-13, 2002, Piscataway, NJ USA, IEEE, Dec. 11, 2002, pp. 141-144, xp010662258, ISBN: 978-0-7803-7571-0.

International Search Report and Written Opinion mailed Apr. 17, 2013 in corresponding International Application No. PCT/US2013/021102.

Liu Feng-qi et al; "Strain— Compensated InGaAs/InAlAs Quantum Cascade Laser"; Journal of Semiconductor, vol. 21, issue 10; Oct. 31, 2000.

Li Aizhen; "The Invention and Advancement on Unipolar Quantum Cascade Lasers"; Chinese Journal of Lasers, vol. 37, issue 9; Sep. 30, 2010.

Zhang Quansheng et al "Investigation on InGaAs/InAlAs Quantum Cascade Lasers"; Journal of Infrared & Millimeter Waves, vol. 20, issue 1; Feb. 28, 2001.

Liu Feng-qi et al "Infrared Quantum Cascade Lasers"; Physics, vol. 30, issue 10; Dec. 31, 2001.

Chinese Office Action entitled, "Notice on the First Office Action (PCT Application in the National Phase)", dated May 13, 2016, and Search Report for corresponding international application in China, Application No.: 201380005249.5.

\* cited by examiner

MID-IR MULTIWAVELENGTH CONCATENATED DISTRIBUTED-FEEDBACK LASER WITH AN ACTIVE CORE MADE OF CASCADED STAGES

This application claims the benefit of priority under 35 U.S.C. §119 of U.S. Prov. Appl. Ser. No. 61/586,327 filed on Jan. 13, 2012, the content of which is relied upon and incorporated herein by reference in its entirety.

FIELD

The present specification generally relates to semiconductor-based lasers and, more specifically, to distributed feedback lasers in the mid-infrared region that have an active core made of cascaded stages to generate several wavelengths simultaneously or sequentially. Methods of making and using such devices are also disclosed.

TECHNICAL BACKGROUND

Distributed feedback ("DFB") lasers are a solid state diode laser technology that incorporates a diffraction grating into the active region of the laser. The DFB design allows for the emission of stable, single wavelengths that are slightly tunable via temperature change. DFB lasers are widely used in optical communication applications where the device's precise and stable wavelength is critical. However, the limited tunability of DFB lasers presents a number of problems and limits the overall usefulness of the devices in other fields. It would be advantageous in fields such as infrared countermeasures, gas sensing, communications, and other applications, if the strengths of DFB lasers could be expanded across a broader range of wavelengths.

SUMMARY

A first embodiment comprises a laser comprising a gain material comprising at least two, compositionally non-identical, layers forming a superlattice; an optical waveguide comprising two ends coated with an anti-reflection material; and at least two laser sections comprising quarter wave shifted gratings placed in series, wherein the gratings have non-equivalent periods or Bragg wavelengths and wherein the laser sections are separated by an electrical isolation region. In some embodiments, the gain material generates photons by intersubband transitions. In some embodiments, the lasing sections are separated by an electric isolation region comprising a p-type layer in an n-cladding layer or by removal of the highly doped part of the n-cladding layer. In some embodiments, the emission wavelength from at least one of the laser sections is from about 2.5 μm to about 15 μm. In some embodiments, at least one layer of the superlattice comprises $Ga_xIn_{1-x}As$, where x is from 0 to 1. In some embodiments, at least one layer of the superlattice comprises $Al_yIn_{1-y}As$, where y is from 0 to 1. In other embodiments, the active region comprises at least three active stacks. In some embodiments, the laser sections lase in pulsed mode. In some embodiments, the laser pulse duration is from about 10 ns to about 1 ms. In other embodiments, the laser sections lase in continuous mode. In some embodiments, all laser sections may fire simultaneously. In some embodiments, the laser sections are fired sequentially.

A second embodiment comprises a method of detecting the signal output from a sample, comprising applying at least one laser event from an embodiment to the sample; and collecting at least some of the light after it has interacted with the sample. In some embodiments the laser wavelength is in the mid-infrared region. In some embodiments, the collecting of the light provides information on mid-infrared absorbance of the sample. In some embodiments, the sample is in the gas or liquid phase. In some embodiments, the collecting of the light provides information on mid-infrared reflectance of the sample. In some embodiments, the sample is in the solid or liquid phase.

DETAILED DESCRIPTION

The present invention can be understood more readily by reference to the following detailed description, drawings, examples, and claims, and their previous and following description. However, before the present compositions, articles, devices, and methods are disclosed and described, it is to be understood that this invention is not limited to the specific compositions, articles, devices, and methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its currently known embodiments. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Disclosed are materials, compounds, compositions, and components that can be used for, can be used in conjunction with, can be used in preparation for, or are embodiments of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of substituents A, B, and C are disclosed as well as a class of substituents D, E, and F, and an example of a combination embodiment, A-D is disclosed, then each is individually and collectively contemplated. Thus, in this example, each of the combinations A-E, A-F, B-D, B-E, B-F, C-D, C-E, and C-F are specifically contemplated and should be considered disclosed from disclosure of A, B, and/or C; D, E, and/or F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and/or C; D, E, and/or F; and the example combination A-D. This concept applies to all aspects of this disclosure including, but not limited to any components of the compositions and steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In this specification and in the claims which follow, reference will be made to a number of terms which shall be defined to have the following meanings:

"Include," "includes," or like terms means encompassing but not limited to, that is, inclusive and not exclusive.

The term "about" references all terms in the range unless otherwise stated. For example, about 1, 2, or 3 is equivalent to about 1, about 2, or about 3, and further comprises from about 1-3, from about 1-2, and from about 2-3. Specific and preferred values disclosed for compositions, components, ingredients, additives, and like aspects, and ranges thereof, are for illustration only; they do not exclude other defined values or other values within defined ranges. The compositions and methods of the disclosure include those having any value or any combination of the values, specific values, more specific values, and preferred values described herein.

The indefinite article "a" or "an" and its corresponding definite article "the" as used herein means at least one, or one or more, unless specified otherwise.

As used herein, a "superlattice" comprises at least two semiconductor materials with different bandgaps that produce quantum well confinement and intersubband transition (see, e.g., U.S. Appl. No. 61/564,375, herein incorporated by reference in its entirety). The thicknesses of the at least two semiconductor materials may change within lattice or may be of constant thickness. If the thicknesses of the materials change, they may change in a linear or nonlinear fashion.

As used herein, a "stage" comprises a series of quantum wells formed by the superlattice that allow electrons to transition from an injector region to an active section. As used herein, a "stack" comprises a series of stages. The "active region" or "core" is comprised of at least one stack and is used to describe the region of the laser that produces the light emission.

A first embodiment comprises a multi-wavelength concatenated DFB ("cDFB") laser with an active core made of a series of cascaded stages to generate multiple wavelengths simultaneously or sequentially in time. In some embodiments, the cDFB laser lases in the infrared ("IR") region. In some embodiments, the cDFB lases in the region from about 2.5 µm to about 15 µm. Such a device is capable of sampling a broad absorption line of a single molecule or several absorption lines from different molecules. Methods of forming embodiments may comprise using a fabrication process similar to that used in distributed feedback ("DFB") quantum cascade lasers ("QCLs"). Embodiments herein are advantageous in that they can replace wavelength tunable external cavity ("EC") QCLs due to smaller sizes, faster speeds and lower costs. Further, embodiments also have size and cost advantages over a DFB QCL arrays because DFB QCL arrays need optical combining optics to combine the output of an array into one optical beam.

Figure 1:
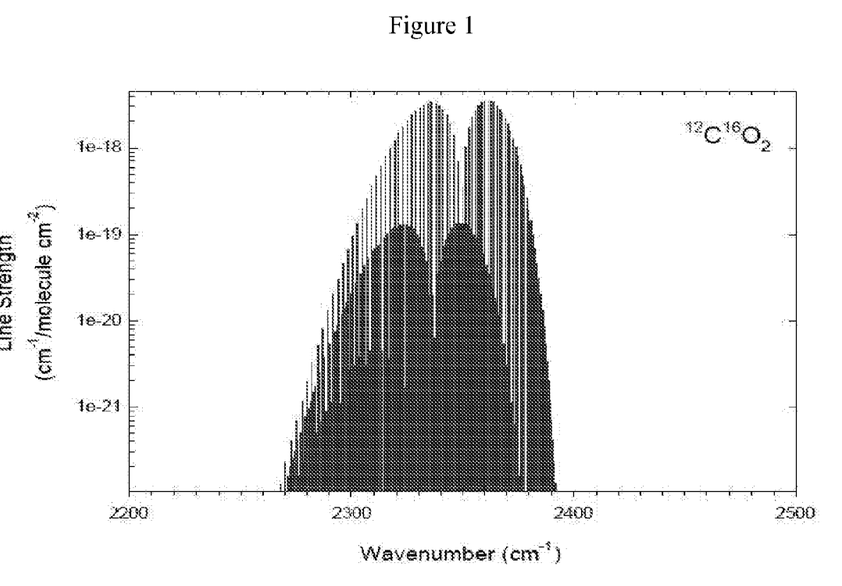
FIG. 1. Absorption spectrum of $CO_2$ near 2350 $cm^{-1}$.
Figure 2:
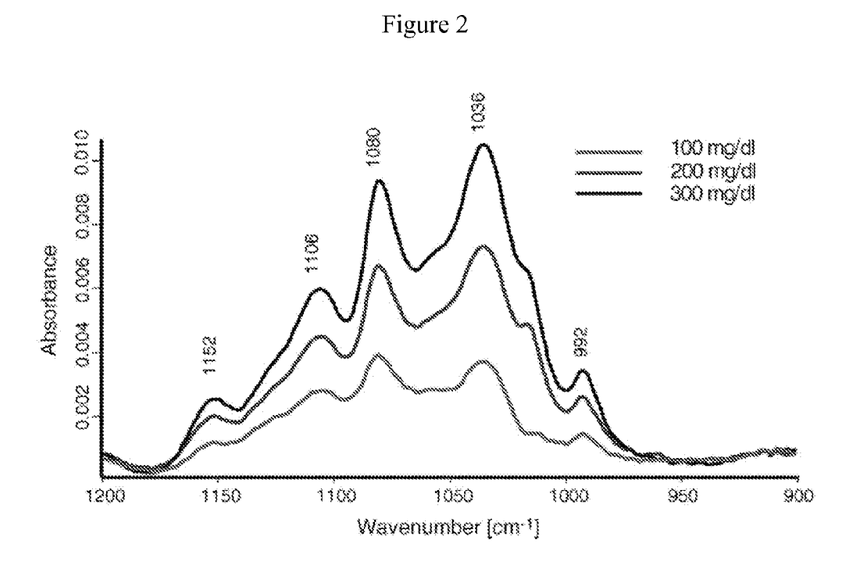
FIG. 2. Absorption spectrum of glucose at three different concentrations.
Figure 3:
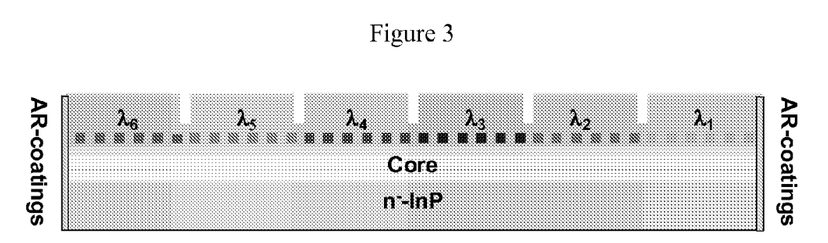
FIG. 3. An embodiment comprising a mid-IR multiwavelength concatenated DFB QCL with an active core made of cascaded stages.

One particular application where embodiments may be useful is in chemical analysis via infrared ("IR") spectroscopy. The strong absorption lines in the mid-IR region from the vibration of chemical bonds can be used to identify molecular composition. Mid-IR wavelength tunable sources like DFB QCLs may be used to scan the wavelength around an absorption line. While traditional DFB QCLs have a small wavelength tuning range of about 10 cm$^{-1}$ and are often used to detect one of narrow absorption lines, such as that of a small molecule (as an example, FIG. 1 shows the absorption lines of $CO_2$ near 2350 cm$^{-1}$, i.e. around 4.2-4.3 µm), embodiments of the present invention have much larger wavelength coverage and may be used to detect the broad absorption line of a large molecule (FIG. 2 shows the absorption at 950-1200 cm$^{-1}$ of glucose).

Figure 6:
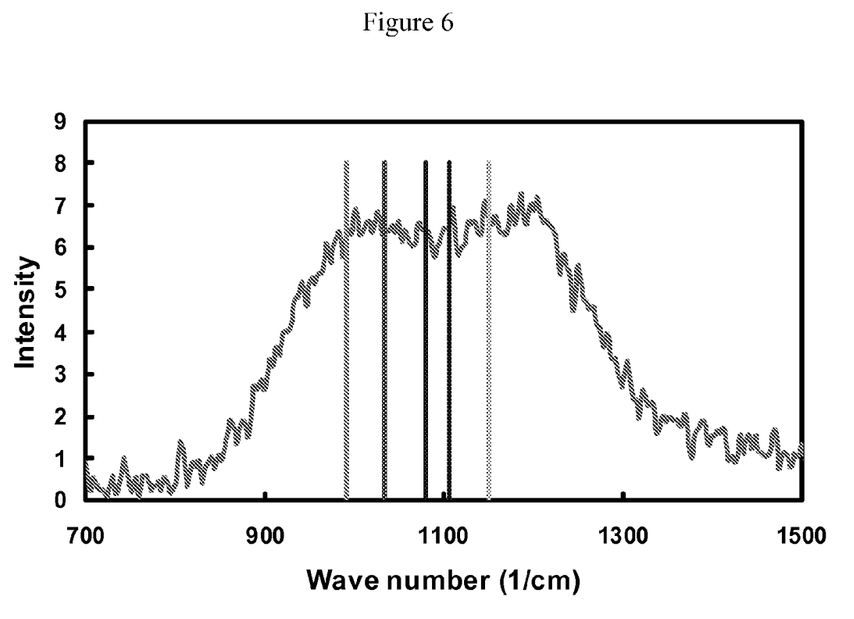
FIG. 6. Spontaneous emission spectrum from a stack of QC cores. The gain peak of each core is designed to be near one of the sampling wavelengths.

The core provides the optical gain needed to achieve lasing. The core of the laser may comprise a stack of quantum cascade ("QC") or interband cascade ("IC") regions. Any QC or IC structure with broad optical gain may be used. In some embodiments, the core comprises a QC structure. In some embodiments, the core comprises an IC structure. The gain peak of each core is designed to be near one of the sampling wavelengths, as shown in FIG. 6. The cores with optical gain at shorter wavelength normally should be placed closer to the center of the optical mode since the optical mode of shorter wavelength is narrower than that of longer wavelength.

Embodiments may comprise a gain material comprising at least two, compositionally non-identical, layers forming a superlattice. By proper design of the layer thicknesses, it is possible to engineer a population inversion between two subbands in the system which is necessary to achieve laser emission. The thickness of the layers may be identical or may be different depending on the desired design. In some embodiments, the layers have a thickness from about 1 Å to about 500 Å. In some embodiments, the layers have a thickness from about 10 Å to about 100 Å. In some embodiments, the layers have a thickness of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200, 250, 300, 350, 400, 450, or 500 Å.

Materials that may be used to form the layers in the gain material generally comprise semiconductors, such as group IV, III-V, and II-VI semiconductors. In some embodiments, the layers may comprise GaAs, $Al_xGa_{1-x}As$, $Si_xGe_{1-x}$, or $Ga_xIn_{1-x}As$ and $Al_yIn_{1-y}As$, wherein x and y are from 0 to 1.

The superlattice gain material may be produced using various techniques, for example molecular-beam epitaxy (MBE) (including gas-source MBE and MO-MBE), metalorganic vapor phase epitaxy (MOVPE), or sputtering. These methods allow production of layers with thicknesses of only a few atomic spacings.

Embodiments may further comprise an optical waveguide. An optical waveguide, as used herein, comprises a physical structure that guides electromagnetic waves in the optical spectrum. While not limited to any specific type of waveguide, one type of optical waveguide commonly used is a ridge waveguide. A ridge waveguide is created by etching parallel trenches in the quantum cascade gain material to create an isolated stripe of QC material, typically, but not necessarily, about 10 μm wide and several mm long (the length is usually defined by cleaving). Lateral mode confinement may be achieved by the deposition in the trenches of a dielectric material, and then the entire ridge is typically coated with gold to provide electrical contact and to help remove heat from the ridge when it is producing light. More commonly, lateral mode confinement is achieved by growing in the trenches a semi-insulating material such as InP if the laser was grown on InP substrate. Light is emitted from the cleaved ends of the waveguide.

Embodiments may further comprise an antireflection or antireflective (AR) layer. As used herein an AR layer comprises an optical coating applied to at least one end (facet) of the device and that reduces reflection, particularly in the IR region. The AR layers may be of any type, such as index-matching, single layer interference, multi-layer interference, or moth eye (nanostructured). In some embodiments, the AR coatings provide less than about 10%, 5%, 4%, 3%, 2%, 1%, 0.5%, 0.1%, 0.01%, 0.001%, or 0% loss.

Embodiments further comprise at least two laser sections placed in series, each laser section comprising a quarter wave shifted grating, wherein the gratings have non-equivalent periods or Bragg wavelength. A grating, as used herein comprises a structure formed from multiple layers of alternating materials with varying refractive index, or by periodic variation of some characteristic (such as height), resulting in periodic variation in the effective refractive index in the guide. Each layer boundary causes a partial reflection of an optical wave. For waves whose wavelength is close to two times the multiplication of the period and the effective refractive index, the many reflections combine with constructive interference, and the grating acts as a high-quality reflector.

The use of quarter-wave shifted, distributed feedback resonators in diode lasers is advantageous as they provide a resonance at the center of the grating stopband that is of higher Q than the resonances to either side. The narrowband resonance of a quarter wave shifted DFB transmission resonator has a Lorentzian response. The theory and use of quarter wave shifted resonators can be found in H. Haus and Y. Lai, *Theory of Cascaded Quarter Wave Shifted Distributed Feedback Resonators*, 28(1) IEEE J. QUANTUM ELEC. 205-213 (1992), herein incorporated by reference in its entirety.

Figure 4:
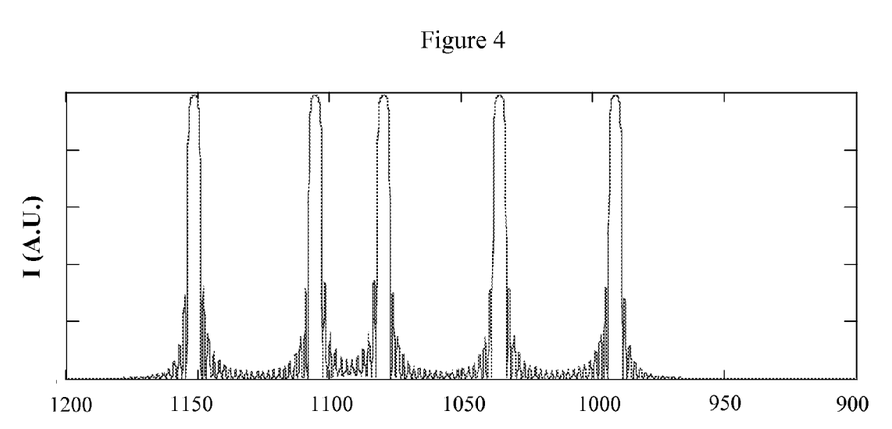
FIG. 4. Reflection spectrum of five gratings in series with five different periods selected to match five absorption peaks of glucose shown in FIG. 2.
Figure 5:
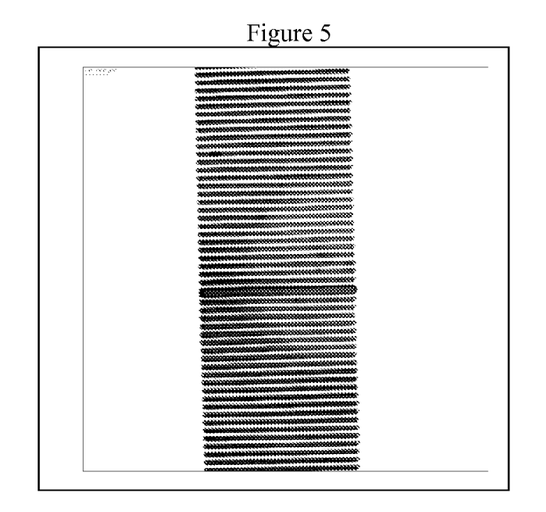
FIG. 5. A picture showing detail of the quarter wavelength shifted grating for one of the DFB sections of an embodiment of the concatenated DFB ("cDFB") laser.

Gratings with multiple periods can be patterned by electron beam ("e-beam") writing or contact printing of a grating mask manufactured by e-beam lithography. FIG. 4 shows the five reflection peaks of five gratings in series with five different periods selected to match five absorption peaks of glucose shown in FIG. 2.

Additional components that may be found in embodiments comprise n-type cladding layers both above and/or below the gain material. The active gain and wavelength selective sections may be capped with a patterned electrical contact layer which comprises respective control electrodes dedicated to the different laser sections. An insulating dielectric material may be deposited in appropriate regions in the patterned electrical contact layer to isolate electrically the distinct regions of the laser structure.

In some embodiments, the lasing sections are separated by a p-type electrical isolation region, as described in U.S. application Ser. No. 13/050,026, incorporated by reference herein in its entirety. For example, an active waveguide core may be sandwiched between upper and lower n-type cladding layers. The active core and the lower n-type cladding layer, as well as at least part of the upper cladding layer, extend through the electrically isolated laser sections of the embodiment. A portion or portions of the upper n-type cladding layer comprise sufficient p-type dopant to define p-type electrical isolation region(s), which extend across part of the thickness of the upper n-type cladding layer along a projection separating the sections of the embodiment. The upper and lower n-type cladding layers may comprise InP, GaAs, AlGaAs, or any other conventional or yet-to-be developed cladding material suitable. For example, and not by way of limitation, it is contemplated that a variety of cladding materials might be suitable, including II-VI semiconductors, Si—Ge or GaN-based materials, etc.

There are diverse ways of realizing the p-type isolation regions. Among these are selective growth, ion implantation, and diffusion of a p-type dopant. If the last option is chosen, the respective compositions of the upper and lower n-type cladding layers and the gain material may be selected to facilitate formation of the p-type electrical isolation regions by dopant diffusion. More specifically, the upper and lower n-type cladding layers may comprise InP and the p-type dopant may be selected such that its maximum stable concentration in the InP upper n-type cladding layer is below approximately $n \times 10^{18}$ cm$^{-3}$, where n is less than 3.

An alternative method of isolating the lasing sections comprises removal of the highly doped part of the n-cladding layer.

By way of example, and not limitation, it is alternatively contemplated that the upper and lower n-type cladding layers may be GaAs-based cladding layers. Some of the cladding layers may be AlGaAs or (Al)GaInP instead of simply GaAs or InP. For GaAs-based cladding layers, the core may be GaAs/AlGaAs, AlGaAs/AlGaAs, (Al)GaInP/(Al)GaInP, or GaInAs/(Al)GaAs. Additional layers of similar composition are contemplated for the remaining layers of the structure and should be selected to compensate for any lattice-mismatch between GaInAs and the GaAs substrate. For example, and not by way of limitation, other possible layers are GaInP, AlGaInP, GaAsP, and GaInAsP. For GaAs-based cladding layers, suitable dopants used to make (Al)GaAs semi-insulating include, but are not limited to Cr and O. At very low temperature growth, semi-insulating (Al)GaAs can be obtained without any dopant.

Embodiments herein may be used in either a pulsed or continuous-wave mode. Laser pulse duration may be from about 1 ns to about 1 ms. In some embodiments, the pulse width at FWHM is about 1 ns, 2 ns, 3 ns, 4 ns, 5 ns, 6 ns, 7 ns, 8 ns, 9 ns, 10 ns, 20 ns, 50 ns, 60 ns, 70 ns, 80 ns, 90 ns, 100 ns, 200 ns, 300 ns, 400 ns, 500 ns, 600 ns, 700 ns, 800 ns, 900 ns, 1 μs, 10 μs, 100 μs, or 1 ms. In some embodiments, devices embodied herein may be designed to fire all laser sections simultaneously, individually, and/or in a sequential or programmed order.

As embodiments herein incorporate aspects of an external cavity quantum cascade laser, the breadth of laser wavelengths that may be output from the devices is significantly greater than what one would expect from a DFB laser. DFB QCLs generally have a small tunability of around 10 cm$^{-1}$. The embodiments described herein have tunabilities over 100 cm$^{-1}$, over 200 cm$^{-1}$, over 300 cm$^{-1}$, over 400 cm$^{-1}$, or over 500 cm$^{-1}$. In some embodiments, the cDFBs embodiments have tunabilities from about 100 cm$^{-1}$ to about 500 cm$^{-1}$.

The peak wavelength of the laser sections may be selected to be the sampling wavelengths ($\lambda_{si}$, I=1 to n) of a broad absorption line of one molecule or several absorption lines from different molecules. In some embodiments, the cDFB lases in the region from about 2.5 μm to about 15 μm. In some embodiments, the cDFB lases at about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0 μm.

Embodiments may be used in any number of methods wherein IR radiation, and particular IR laser radiation would be advantageous. Particular applications include IR absorbance or reflectance measurements, IR and FTIR spectroscopies, Raman spectroscopy, gas and/or chemical weapons detection, chemical dynamics and kinetics measurements, thermal experiments, etc. In one embodiment, the embodiments are used in IR absorbance measurements to identify molecular compositions.

EXAMPLES

Example 1

Figure 7:
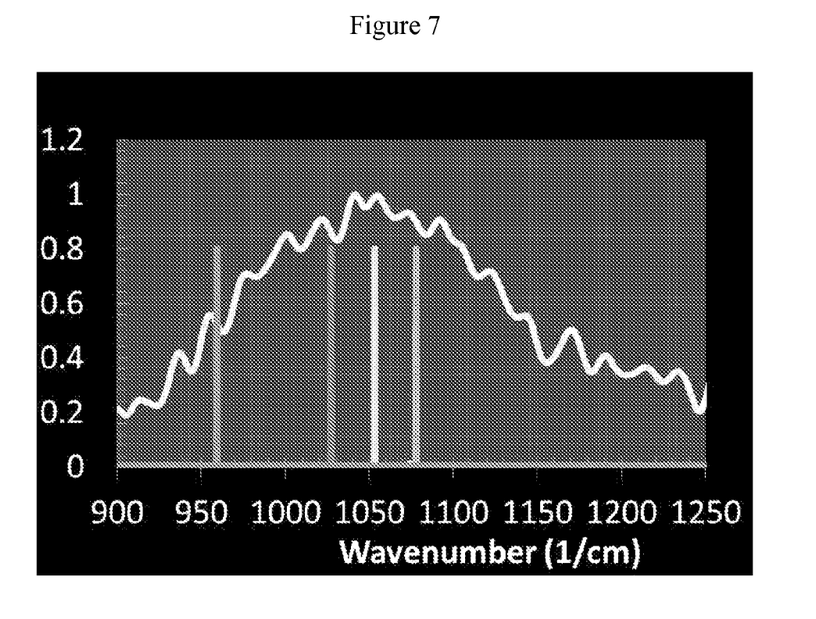
FIG. 7. Electroluminescence spectrum from the core as compared to the lasing spectra from four different DFB quantum cascade lasers ("QCLs") in a cDFB embodiment fabricated from the same wafer.

The spectra shown in FIG. 7 were obtained from a cDFB laser with a core made of three active stacks. The electroluminescence spectrum from the core shown as "(a)" indicates the gain spectrum. Four lasing spectra shown as curves "(b)", "(c)", "(d)", and "(e)" are the lasing spectra from four different laser sections fabricated in the same wafer.

Example 2

Figure 8:
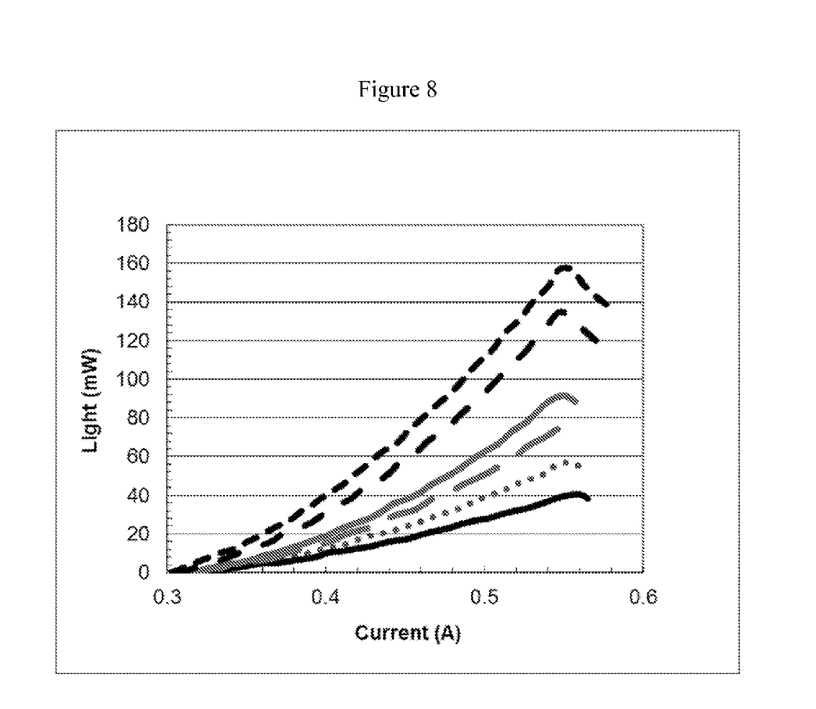
FIG. 8. Pulsed light-current curves of the second DFB QCL as a function of DC bias in the first DFB QCL next to the front facet. The bias was 11V (black, close dash; ---); 10V (black, spaced dash; - - -); 9V (grey solid; ······); 8V (grey, long spaced dash; ········); 4V (grey dot; •••); and 0V (black solid; —).

The pulsed light-current curves (FIG. 8) of the second laser section in the cDFB were also measured as a function of DC bias in the first laser section (i.e., next to the front facet). The biases shown were at 11V (black, close dash; ---); 10V (black, spaced dash; - - -); 9V (grey solid; ⋯⋯); 8V (grey, long spaced dash; ⋯ ⋯ ⋯); 4V (grey dot; •••); and 0V (black solid; —). The output power from the second laser section increases with increased DC bias because of reduced optical loss through the cavity of the first laser section. The power consumption of DC bias can be kept to low (~0.1 W) because the current is less than 0.12 A at 9V. The power consumption can be further reduced by using pulsed bias.

Example 3

Figure 9:
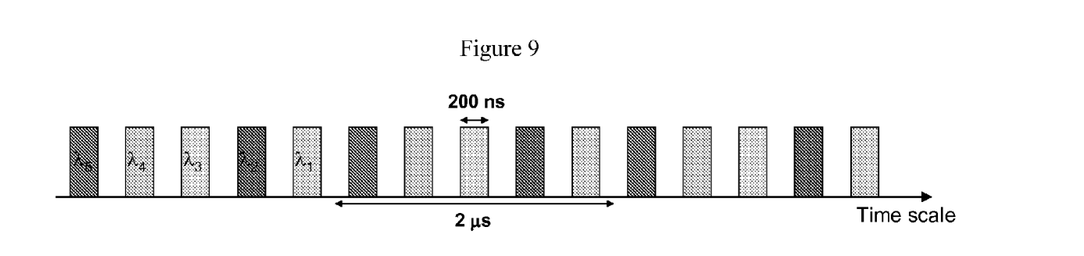
FIG. 9. Example sequential operation of the cDFB to minimize thermal heating of the device and allow multiple sampling wavelengths.

To minimize the heating within a pulse and from the neighboring pulses applied to the same laser section, we propose the following time sequential operation as shown in FIG. 9 and the pulse width on the order of a few hundred nanosecond or less, for example 200 ns, to keep the core temperature rise to less than 20° C. During the time sequential operation shown in FIG. 9, in order to minimize the optical loss of the output from any laser section in concatenation through the laser sections in the front of it, the laser sections should be DC or pulse biased below threshold when they are not required to be in lasing mode. This will minimize feedback stemming from the non-lasing laser stage as noted in Li et al., 36 (10) *IEEE Journal of Quantum Electronics*, 1110-1116 (2000), herein incorporated by reference in its entirety.

We claim:
1. A laser comprising:
   a. a gain material comprising at least two, compositionally non-identical, layers forming a superlattice, wherein the gain material generates photons by intersubband transitions;
   b. an optical waveguide comprising two ends coated with an anti-reflection material; and
   c. at least two lasing sections placed in series, wherein each lasing section comprises a grating, wherein the gratings have non-equivalent periods or Bragg wavelengths, and wherein the lasing sections are separated by an electrical isolation region,
   wherein the grating comprises quarter wave shifted gratings;
   wherein the lasing sections are separated by:
   an electrical isolation region comprising a p-type dopant with maximum stable concentration in an InP upper n-type cladding layer below approximately n×10$^{18}$ cm$^{-3}$, where n is less than 3; or
   removal of a high doping part of an n-cladding layer.
2. The laser of claim 1, wherein the emission wavelength from at least one of the laser sections is from about 2.5 μm to about 15 μm.
3. The laser of claim 1, wherein at least one layer of the superlattice comprises Ga$_x$In$_{1-x}$As, where x is from 0 to 1.
4. The laser of claim 1, wherein at least one layer of the superlattice comprises Al$_y$In$_{1-y}$As, where y is from 0 to 1.
5. The laser of claim 1, wherein an active region of the laser comprises at least three stacks wherein the stacks with laser sections at the shortest wavelengths are placed in the center of the device.
6. The laser of claim 1, wherein the laser sections lase in pulsed mode.
7. The laser of claim 6, wherein the laser pulse width is from about 10 ns to about 1 ms.
8. The laser of claim 1, wherein the laser sections lase in continuous mode.
9. The laser of claim 1, wherein all laser sections may fire simultaneously.
10. The laser of claim 1, wherein the laser sections are fired sequentially.
11. A method of detecting the signal output from a sample comprising:
   a. applying at least one laser event to the sample; and
   b. collecting at least some of the light after it has interacted with the sample, wherein the at least one laser event is from a laser comprising:
   a gain material comprising at least two, compositionally non-identical, layers forming a superlattice, wherein the gain material generates photons by intersubband transitions;
   an optical waveguide comprising two ends coated with an anti-reflection material; and
   at least two lasing sections placed in series, wherein each lasing section comprises a grating, wherein the gratings have non-equivalent periods or Bragg wave- lengths, and wherein the lasing sections are separated by an electrical isolation region, wherein the grating comprises quarter wave shifted gratings;

wherein the lasing sections are separated by:
an electrical isolation region comprising a p-type dopant with maximum stable concentration in an InP upper n-type cladding layer below approximately $n \times 10^{18}$ cm$^{-3}$, where n is less than 3; or
removal of a high doping part of an n-cladding layer.

12. The method of claim 11, wherein the laser wavelength is in the infrared region.

13. The method of claim 12, wherein the collecting of the light provides information on infrared absorbance of the sample.

14. The method of claim 11, wherein the sample is in the gas phase.

15. The method of claim 11, wherein the sample is in the liquid phase.

16. The method of claim 11, wherein the sample is in the solid phase.

17. The method of claim 11, wherein the collecting of the light provides information on infrared reflectance of the sample.

* * * * *